United States Patent
Lange

(10) Patent No.: US 7,288,114 B2
(45) Date of Patent: *Oct. 30, 2007

(54) MEDICAL IMPLANT

(75) Inventor: Robert Lange, Paris (FR)

(73) Assignee: Co-Ligne AG, Zurich (CH)

( * ) Notice: Subject to any disclaimer, the term of this patent is extended or adjusted under 35 U.S.C. 154(b) by 149 days.

This patent is subject to a terminal disclaimer.

(21) Appl. No.: 10/469,118

(22) PCT Filed: Feb. 26, 2002

(86) PCT No.: PCT/CH02/00111

§ 371 (c)(1),
(2), (4) Date: Mar. 23, 2004

(87) PCT Pub. No.: WO02/067822

PCT Pub. Date: Sep. 6, 2002

(65) Prior Publication Data

US 2004/0158324 A1    Aug. 12, 2004

(30) Foreign Application Priority Data

Feb. 27, 2001   (EP) .................................. 01810202

(51) Int. Cl.
*A61F 2/44* (2006.01)
(52) U.S. Cl. ................................ 623/17.11; 623/23.51; 606/76.1
(58) Field of Classification Search ................ 428/224, 428/227, 229, 245, 257, 288, 292.1; 623/17.11, 623/23.51; 606/76
See application file for complete search history.

(56) References Cited

U.S. PATENT DOCUMENTS

| | | | | |
|---|---|---|---|---|
| 3,875,595 A | * | 4/1975 | Froning | 623/17.12 |
| 4,309,777 A | * | 1/1982 | Patil | 623/17.13 |
| 4,401,112 A | * | 8/1983 | Rezaian | 606/61 |
| 4,501,269 A | * | 2/1985 | Bagby | 606/61 |
| 4,554,914 A | * | 11/1985 | Kapp et al. | 606/61 |
| 4,627,853 A | * | 12/1986 | Campbell et al. | 128/898 |
| 4,636,217 A | * | 1/1987 | Ogilvie et al. | 623/17.11 |
| 4,678,470 A | * | 7/1987 | Nashef et al. | 623/23.63 |
| 4,714,469 A | * | 12/1987 | Kenna | 606/61 |
| 4,743,256 A | * | 5/1988 | Brantigan | 128/898 |
| 4,759,769 A | * | 7/1988 | Hedman et al. | 623/17.13 |
| 4,834,757 A | * | 5/1989 | Brantigan | 623/17.11 |
| 4,863,476 A | * | 9/1989 | Shepperd | 623/17.15 |
| 4,878,915 A | * | 11/1989 | Brantigan | 623/17.11 |

(Continued)

FOREIGN PATENT DOCUMENTS

FR          2 727 003         5/1996

(Continued)

*Primary Examiner*—N. Edwards
(74) *Attorney, Agent, or Firm*—Browdy and Neimark, PLLC

(57) ABSTRACT

The medical implant is constructed of a fiber reinforced plastic. That fibers (50a, 50b) are generally aligned in layers (C, D, E), wherein the fibers of at least two different layers having different orientations. The fibers are long and oriented in relationship to the biomechanical requirements. The implant can oppose multi-directional forces and can be manufactured with the appropriate strength and stiffness.

12 Claims, 3 Drawing Sheets

U.S. PATENT DOCUMENTS

| | | | |
|---|---|---|---|
| 4,932,975 A * | 6/1990 | Main et al. | 623/17.12 |
| 5,015,247 A * | 5/1991 | Michelson | 606/61 |
| 5,026,373 A * | 6/1991 | Ray et al. | 606/61 |
| 5,055,104 A * | 10/1991 | Ray | 606/61 |
| 5,059,193 A * | 10/1991 | Kuslich | 606/61 |
| 5,062,850 A * | 11/1991 | MacMillan et al. | 623/17.11 |
| 5,147,402 A * | 9/1992 | Bohler et al. | 623/16.11 |
| 5,181,930 A * | 1/1993 | Dumbleton et al. | 623/23.34 |
| 5,192,327 A * | 3/1993 | Brantigan | 623/17.11 |
| 5,236,460 A * | 8/1993 | Barber | 623/17.15 |
| 5,263,953 A * | 11/1993 | Bagby | 606/61 |
| 5,429,863 A * | 7/1995 | McMillin | 428/370 |
| 5,607,424 A | 3/1997 | Tropiano | |
| 6,800,092 B1 * | 10/2004 | Williams et al. | 623/17.11 |
| 2002/0123750 A1 * | 9/2002 | Eisermann et al. | 606/69 |
| 2004/0049270 A1 * | 3/2004 | Gewirtz | 623/17.11 |

FOREIGN PATENT DOCUMENTS

| | | |
|---|---|---|
| GB | 1 363 305 | 8/1974 |

* cited by examiner

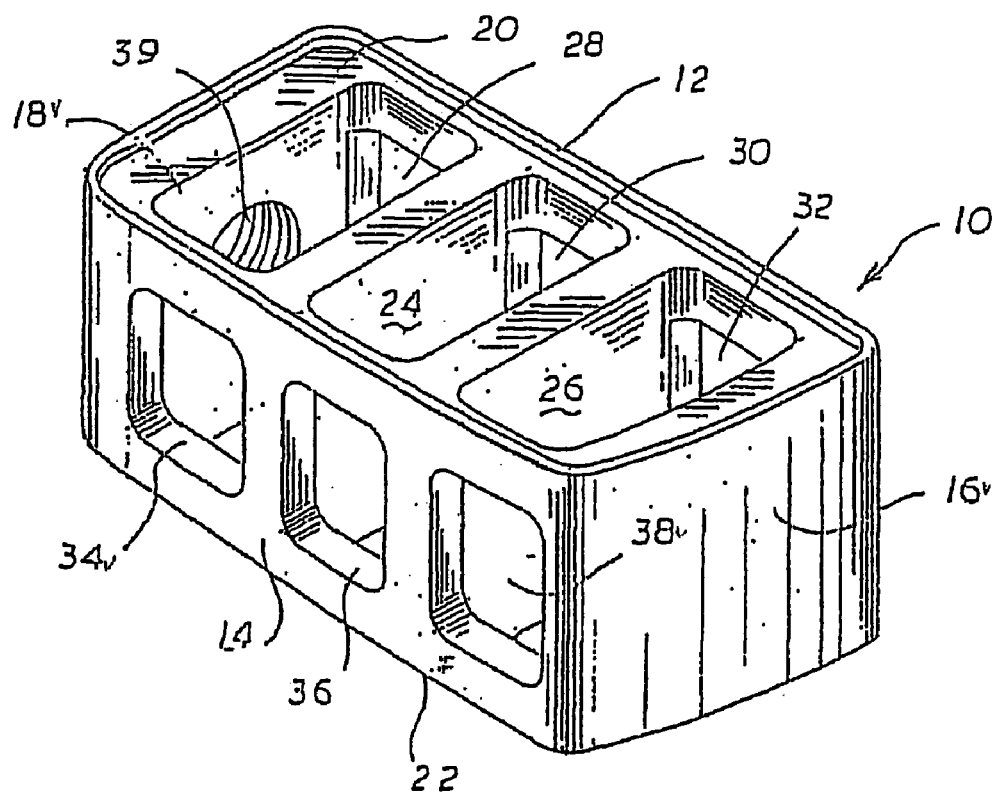
FIG_1
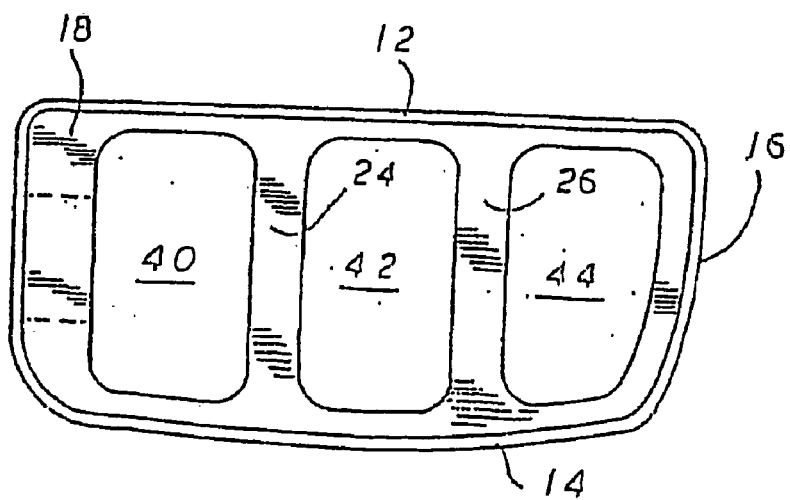
FIG_2

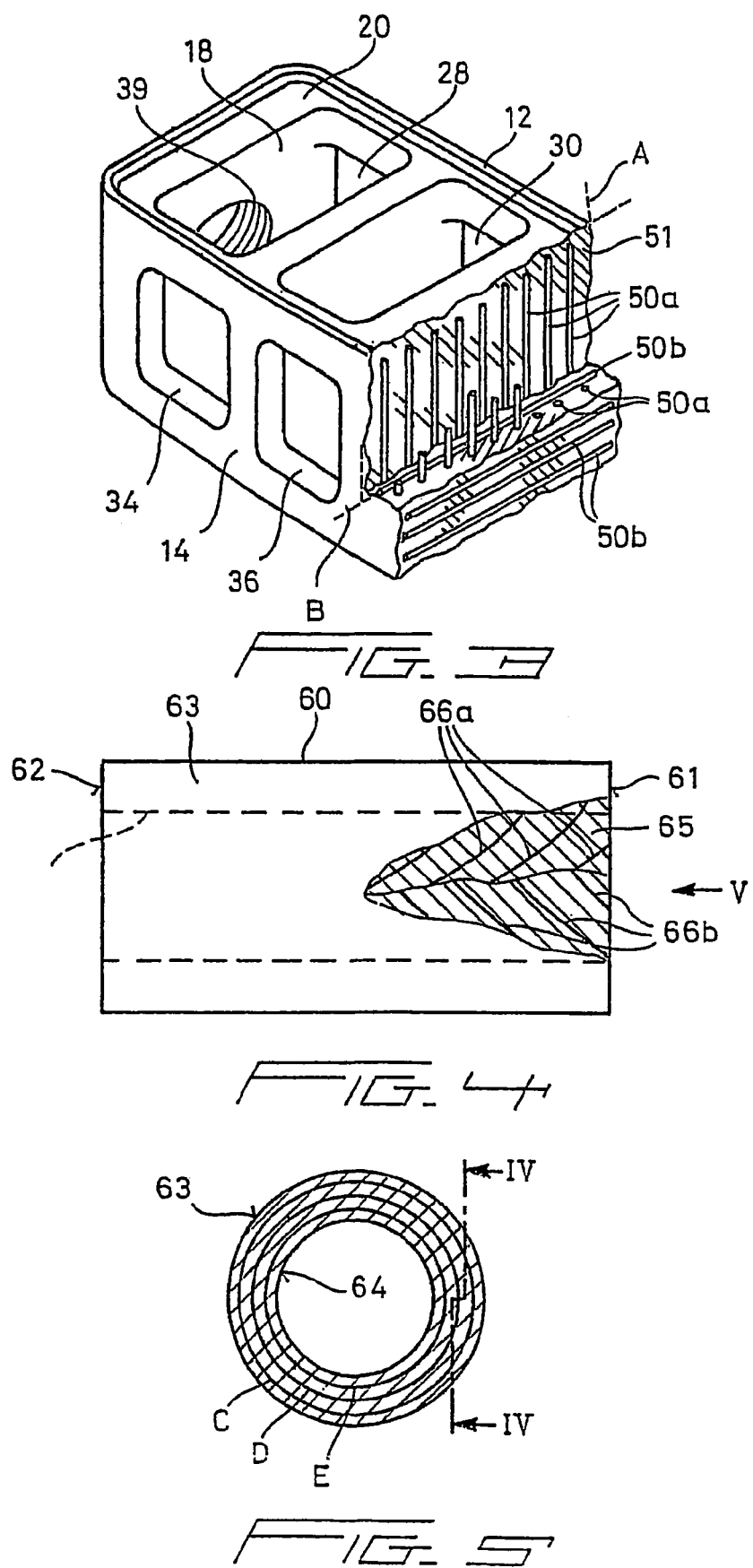

MEDICAL IMPLANT

The invention relates to a medical implant being constructed of a fiber reinforced plastic. The medical implant is preferably an intervertebral cage for use in spinal repair work. Intervertebral cages are utilized to control and fix the spacing between vertebrae and are hollow so as to receive bone fragments which will grow and ultimately join the adjacent vertebrae together as though they were a single unit.

Intervertebral cages have been utilized for this purpose for many years. It is essential that they are hollow but strong enough so that they will never collapse. At the same time, the hollow interiors must have side top and hollow openings. The more bone fragments available and the greater the openings, the quicker vertebrae will be joined together.

The materials used for these cages are coated or uncoated titanium alloys or polymers with or without carbon reinforcement. The carbon composite polymer has two advantages over titanium and other materials used. On the one hand, its radiolucency allows the repair being monitored by standard radiographic methods. On the other, its modulus of elasticity and structure makes it possible to build an implant with stiffness very close to a specific bone. These mechanical characteristics protect the bone graft from degeneration and prevent stress under load.

It is important that an implant meets the following criteria: effectiveness, safety and quality. Effectiveness means that the implant is suitable for the use and the required biolomechanical function. Safety means that there is a minimal health risk for the patient. Quality means that the desired properties are predictable.

It is an object of this invention to provide an improved medical implant which provides a greater stability during a long term implantation and which meets nevertheless the biocompatibility criteria.

The invention permits the manufacture of a sturdy implant and particularly an intervertebral cage of increased strength. By judiciously selecting the orientation of the fibers within the various structural elements, an implant of increased strength can be obtained. The increased strength permits the manufacture of an implant and particularly a cage which has relatively thin but strong walls that will not collapse. A weight bearing structure is subjected to many multi-direction forces. These forces must be opposed with the appropriate strength and stiffness according to specific anatomical structure. The implant according to the present invention has fibers aligned in layers, wherein the fibers of at least two different layers having different orientation. The fibers are oriented in relationship to the requirements noted above and especially to oppose- the multi-direction forces. The fibers are long fibers as a long fiber is stronger than a short one. The fibers may be generally as long as a dimension of the implant. The fibers are not random oriented and are not chopped fibers. It has been demonstrated that bone can regenerate itself according to the physiological loads to which it is subjected. Therefore an implant which can minimise the load of a specific structure will help the regeneration of bone.

Another advantage of the invention described is that, unlike metal cages, there is little or no interference with diagnostic x-rays. Thus, the attending physician can observe postoperative progress much more accurately than with metal cages. It is an important advantage of the invention described, that the implant can be manufactured to meet the biomechanical properties and to resist the specific forces which act on the implant during a long term implantation. These biomechanical forces are rotation, three point bending, shear compression and traction. There may be also combined forces. By varying the orientation and length of the fibers the amount of flexibility and resistance desired can be controlled. In elderly people, the physician will normally select a cage of little flexibility and for younger patients, the physician might select a fiber orientation that permits a flexibility that is more closely associated with the flexibility of the bones of the patient involved.

Other advantages and features of the present invention will be apparent to those skilled in the art after reading the following specification with reference to the accompanying drawings.

BRIEF DESCRIPTION OF THE DRAWINGS

FIG. 1 is a perspective view of a cage of this invention;

FIG. 2 is a side elevation;

FIG. 3 is a perspective view of the cage of this invention with a front part broken away;

FIG. 4 is a side elevation of an alternative embodiment of an implant of this invention, wherein a part is broken away;

FIG. 5 is another side elevation of the implant according to FIG. 4 and

DESCRIPTION OF THE PREFERRED EMBODIMENTS

Figure 6:
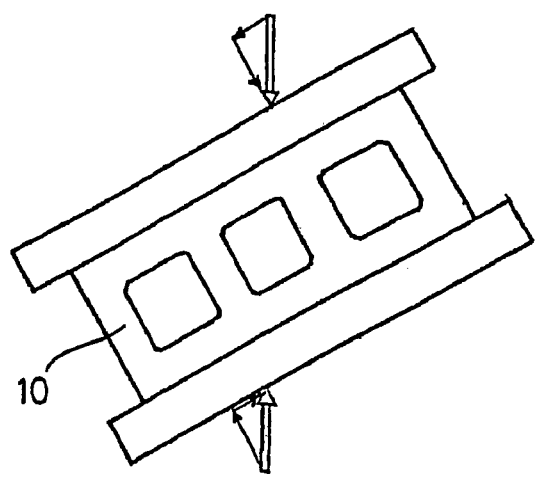
FIG. 6 to 8 are diagrammatic illustrations of the forces which can act on an intervertebral cage.

The cage 10 shown in FIG. 1 to 3 has a front wall 16, a rear surface 18 and a pair of side surfaces 12 and 14. The cage is completed by having a top 20 and a bottom 22.

A pair of interior struts 24 and 26 extend between the sides 12 and 14 and engage the solid part of walls between the side openings. Side 12 has openings 28, 30 and 32, and side 14 has openings 34, 36 and 38. Rear wall 18 has a threaded opening 39 to receive a positioning tool of a type well known to those skilled in the art. Partitions or struts 24 and 26 divide the cage 10 into three compartments or cavities 40, 42, and 44 as shown in FIG. 2. Note the smooth front wall 16 and the other side walls. These walls will not tear or mangle the delicate nerves and blood vessels near the site of the spinal cord.

Figure 7:
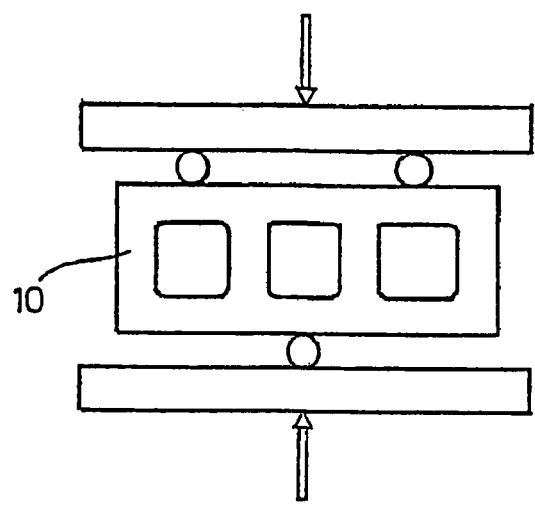
Figure 8:
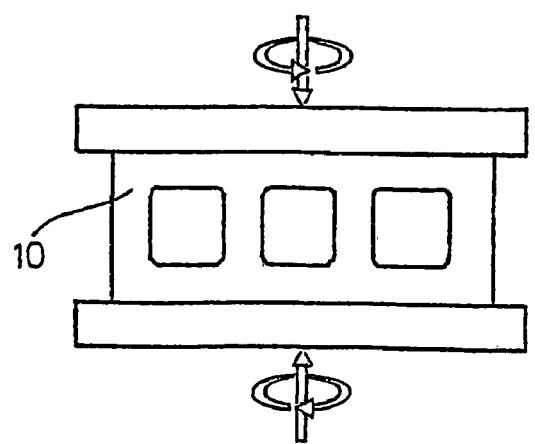

The cage 10 is constructed of a fiber composite. The composite is manufactured by embedding long and aligned fibers 50a and 50b into a matrix. The fibers are preferably carbon fibers and the matrix 51 is preferably PEEK (polyetheretherketone) or PEKEKK (polyetherketoneetherketonelcetone). PEKEKK is sometimes referred in the literature under the name Ultra-Pek. The fibers 50a and 50b are aligned in layers A and B. As FIG. 3 clearly shows, the fibers 50a have an orientation, which is different from the orientation of the fibers 50b. The orientation as well the length of the fibers 50a and 50b are controlled to meet the specific biomechanical requirements of the cage 10. The fibers 50a and 50b are long fibers and are preferably a length between x and y mm. The forces which the cage has to resist are particularly the forces illustrated in FIGS. 6, 7 and 8. FIG. 6 illustrates shear forces acting on cage 10. At least some of the fibers are oriented to resist to these shear forces. FIG. 7 illustrates three-point bending forces and FIG. 8 rotation forces acting on cage 10. The fibers 50a and 50b are oriented to resist at least one of theses forces. Generally the fibers are oriented perpendicular to a force which has to be opposed. As the fibers 50a and 50b have different orientations, they can oppose different forces.

FIG. 4 and FIG. 5 show an implant 60 which has a tubular form and a front surface 65, a rear surface 62, an outer surface 63 and an innerside surface 64. The implant 60 can be an intervertebral cage and is made of a fiber composite and has carbon fibers 66a and 66b embedded in a matrix 65, which preferably is PEEK or PEKEKK. The fibers 66a and 66b are aligned in layers C, D and E which are parallel to the outer surface 60 and to each other. The fibers 66a and 66b have the form of a coil and have different orientations as shown in FIG. 4. The implants described herein take the form of cages, however, they can tale the form of a plate, rod or rail, wherein the fibers are oriented to resist the stress to which the implant will be subjected. The length of the fibers depends on the dimensions of the implant and are preferably as long as possible. If the implant is a rail and fibers are oriented parallel to the longitudinal axis, these fibers can be as long as the rail.

The invention claimed is:

1. A medical implant constructed of a fiber reinforced plastic with the fibers being aligned in at least two layers, the fibers of one of the layers being generally aligned in a first direction, and the fibers of the other layer being oriented in a second direction.

2. An implant according to claim 1, wherein the fibers are oriented in relationship to biomechanical forces which act on the implant.

3. An implant according to claim 1 or 2, characterised in that the fibers are embedded in a matrix.

4. An implant according to claim 3, characterised in that the matrix is PEEK OR PEKEKK.

5. An implant according to claim 1 or 2, characterised in that fibers of a layer have approximately the same length.

6. An implant according to claim 4, characterised in that said implant is a intervertebral cage.

7. An implant according to claim 6, characterised in that said cage comprises a generally hollow elongated shell.

8. Implant according to claim 1 or 2, characterised in that the fibers are carbon fibers.

9. A medical cage implant comprising a generally rectangular outer wall having a front surface,
   a rear surface generally parallel to said front first and second side walls extending therebetween,
   said outer wall having an upper surface and a bottom surface,
   a plurality of struts extending between said first and said second side walls, parallel to said front and rear surface and dividing said implant into a plurality of cavities,
   said side walls having openings communicating with said cavities,
   the fibers in said front wall, said rear wall and said struts being oriented,
   wherein the orientations of the fibers extend in at least two different directions.

10. A medical cage according to claim 9, wherein the fibers of at least one layer are oriented horizontally and fibers of at least one other layer are oriented vertically.

11. An implant according to claim 5, wherein said implant is an intervertebral cage.

12. An implant according to claim 6, wherein said cage has first and second side members, and said side members have struts between said first and second side members.

* * * * *